United States Patent
Safavi et al.

(10) Patent No.: US 12,263,263 B2
(45) Date of Patent: *Apr. 1, 2025

(54) DEVICE AND METHOD FOR STERILIZING AND STORAGE OF LABORATORY CONSUMABLES

(71) Applicant: GRENOVA, INC., Richmond, VA (US)

(72) Inventors: Ali Safavi, Richmond, VA (US); Thomas Patrick Finnigan, Richmond, VA (US)

(73) Assignee: GRENOVA, INC., Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/238,781

(22) Filed: Aug. 28, 2023

(65) Prior Publication Data

US 2023/0405164 A1 Dec. 21, 2023

Related U.S. Application Data

(60) Continuation of application No. 17/174,200, filed on Feb. 11, 2021, now Pat. No. 11,786,617, which is a
(Continued)

(51) Int. Cl.
*A61L 2/10* (2006.01)
*A47L 15/42* (2006.01)
(Continued)

(52) U.S. Cl.
CPC .............. *A61L 2/10* (2013.01); *A47L 15/4242* (2013.01); *B01L 9/543* (2013.01); *B01L 13/02* (2019.08);
(Continued)

(58) Field of Classification Search
CPC ........................................................ A61L 2/10
See application file for complete search history.

(56) References Cited

U.S. PATENT DOCUMENTS

| 4,894,207 A * | 1/1990 | Archer ...................... A61L 2/06 219/400 |
| 10,953,118 B2 * | 3/2021 | Safavi ...................... F26B 3/02 |

(Continued)

OTHER PUBLICATIONS

U.S. Notice of Allowance issued in U.S. Appl. No. 17/174,200 dated May 31, 2023.
(Continued)

*Primary Examiner* — Donald R Spamer
(74) *Attorney, Agent, or Firm* — Welsh Flaxman & Gitler LLC (57) ABSTRACT

A sterilizing storage device may include a housing defining an interior chamber and having an opening defined in the housing to enable access to the interior chamber, the interior chamber divided into a plurality of storage compartments, each storage compartment of the plurality of storage compartments configured to slidably receive a carrier holding a plurality of laboratory consumables. A door may be affixed to the housing and selectively movable between a closed and opened position. A plurality of ultraviolet (UV) lamps may be positioned such that each storage compartment of the plurality of storage compartments receives UV light from a UV lamp of the plurality of UV lamps. At least one fan may draw air into the housing. A plurality of carriers configured to hold the plurality of laboratory consumables suspended from an upper surface of the carrier such that a distal end of each laboratory consumable hangs down into an open interior portion of the carrier. Each carrier having at least one side surface opening and at least one bottom surface opening to enable air flow and UV light to reach the distal end of each laboratory consumable.

8 Claims, 13 Drawing Sheets

Related U.S. Application Data division of application No. 15/863,030, filed on Jan. 5, 2018, now Pat. No. 10,953,118.

(60) Provisional application No. 62/444,863, filed on Jan. 11, 2017.

(51) Int. Cl.
| | |
|---|---|
| *B01L 9/00* | (2006.01) |
| *B08B 7/00* | (2006.01) |
| *B08B 9/00* | (2006.01) |
| *F26B 3/02* | (2006.01) |
| *F26B 3/04* | (2006.01) |
| *F26B 3/28* | (2006.01) |
| *F26B 9/06* | (2006.01) |
| *B01L 3/02* | (2006.01) |

(52) U.S. Cl.
CPC .............. *B08B 7/0057* (2013.01); *B08B 9/00* (2013.01); *F26B 3/02* (2013.01); *F26B 3/04* (2013.01); *F26B 3/283* (2013.01); *F26B 9/066* (2013.01); *A61L 2202/122* (2013.01); *A61L 2202/18* (2013.01); *B01L 3/0275* (2013.01); *B01L 2200/141* (2013.01)

(56) References Cited

U.S. PATENT DOCUMENTS

| | | | |
|---|---|---|---|
| 2003/0034459 | A1* | 2/2003 | Bonin ............... A61L 2/06 250/491.1 |
| 2008/0265179 | A1* | 10/2008 | Havens ............. A61L 2/10 250/492.1 |
| 2010/0044582 | A1* | 2/2010 | Cooper ............. A61L 2/10 250/455.11 |
| 2012/0153783 | A1* | 6/2012 | Shoenfeld .......... A61L 2/10 362/133 |
| 2012/0282135 | A1* | 11/2012 | Trapani ............ A61L 2/24 422/291 |
| 2013/0062534 | A1 | 3/2013 | Cole |
| 2015/0314341 | A1* | 11/2015 | Safavi ............. B01L 3/0275 134/1 |

OTHER PUBLICATIONS

U.S. Appl. No. 17/174,200, filed Feb. 11, 2021, Ali Safavi et al., Grenova, Inc.

* cited by examiner

DEVICE AND METHOD FOR STERILIZING AND STORAGE OF LABORATORY CONSUMABLES

CROSS-REFERENCE TO RELATED APPLICATIONS

This application is a Continuation of U.S. patent application Ser. No. 17/174,200, filed on Feb. 11, 2021, which is a divisional of and claims priority to U.S. patent application Ser. No. 15/863,030, filed Jan. 5, 2018, now U.S. Pat. No. 10,953,118, which claims priority to U.S. Provisional Application Ser. No. 62/444,863, filed Jan. 11, 2017, the contents of which are incorporated herein by reference in their entirety.

FIELD OF THE INVENTION

The present technology relates to laboratory consumables, and more particularly to a device and method for sterilizing and storing laboratory consumables.

BACKGROUND

Every year around 4,000,000 pounds of plastic pipette tips, after a single use, are disposed of in landfills globally, leading to significant environmental pollution and costs. A typical laboratory consumes several thousand pipette tips daily for samples and assay procedures. Due to the lack of options for cleaning plastic consumables, the labs discard pipette tips after each use. Such high consumption of plastic tips adds $25,000-$1.SM to the annual operation cost to each of the approximately 14,000 research laboratories in the US.

Devices that are capable of efficient pipette tip cleaning and sterilization could save businesses substantial amounts of money in their scientific operations and drastically reduce the amount of waste produced in the course of operations. Devices and methods for cleaning and drying pipette tips have been developed by the applicant of the present invention. Such devices and methods are disclosed in the following co-owned patent and patent applications, which are incorporated by reference in their entireties: U.S. Pat. No. 9,421,289, issued Aug. 23, 2016; U.S. patent application Ser. No. 15/189,750, filed Jun. 22, 2016; U.S. patent application Ser. No. 14/796,712, filed Jul. 10, 2015; U.S. patent application Ser. No. 15/042,578, filed Feb. 12, 2016; and U.S. patent application Ser. No. 14/575,374, filed Dec. 18, 2014. These devices and methods for cleaning and drying pipette tips produce large quantities of cleaned pipette tips which may be re-used instead of discarded. However, asl protective packaging for the pipette tips would no longer be available, there is a need for a solution to store the cleaned pipette tips in a manner that helps prevent contamination until the pipette tips are to be used again.

BRIEF SUMMARY OF THE DISCLOSURE

In one embodiment of the invention, a method of sterilizing and storing laboratory consumables comprises slidably receiving a carrier holding a plurality of laboratory consumables into each of one or more of a plurality of storage compartments within an interior chamber defined in a housing, exposing the plurality of laboratory consumables to ultraviolet (UV) light from a UV lamp positioned above each respective storage compartment and from a UV lamp positioned below each respective storage compartment, determining from which of the plurality of storage compartments a carrier should be removed based on for which carrier a longest period of time has elapsed since going through a predefined sterilization procedure, and indicating to a user into which of the plurality of storage compartments a carrier should be placed or indicating to a user from which of the plurality of storage compartments a carrier should be removed.

The method may further comprise detecting a presence of a carrier in a respective storage compartment and detecting whether a door affixed to the housing is open or closed. The plurality of laboratory consumables may be exposed to UV light after one or more carriers have been detected to have been inserted into respective storage compartments and the door has been detected to be closed.

The plurality of laboratory consumables may be exposed to UV light from the UV lamps positioned above and below the respective storage compartments in which the presence of a carrier has been detected.

The plurality of laboratory consumables may be exposed to UV light for a predetermined amount of time.

The method may further comprise deactivating the UV lamps if the door has been detected to be opened and reactivating the UV lamps for a remaining portion of the predetermined period of time when the door has been detected to be closed.

The method may further comprise determining if a carrier has been removed prior to completion of a predefined sterilization procedure and providing a notification to a user.

The method may further comprise drawing air into the housing through an air intake defined in one wall of the housing, drawing or pushing air through the interior chamber, and pushing air out of the housing through an air outflow defined in an opposing wall of the housing.

The method may further comprise providing heat to the interior chamber.

BRIEF DESCRIPTION OF THE SEVERAL VIEWS OF THE DRAWING(S)

The foregoing summary, as well as the following detailed description of the disclosure, will be better understood when read in conjunction with the appended drawings. For the purpose of illustrating the disclosure, there are shown in the drawings embodiments which are presently preferred. It should be understood, however, that the disclosure is not limited to the precise arrangements and instrumentalities shown. In the drawings.

DETAILED DESCRIPTION

Embodiments of the invention comprise devices and methods for storing laboratory consumables, including but not limited to pipette tips. Embodiments of the invention may be used, for example, to store laboratory consumables that were previously used and then cleaned (such as via the devices and methods described in the Background) in a manner that helps prevent contamination until the laboratory consumables are to be used again. Embodiments of the invention may also optionally be used to dry and/or sanitize laboratory consumables. While the devices and methods disclosed herein may be used with any suitable laboratory consumable, embodiments of the invention will be described herein related to use with pipette tips for simplicity.

A laboratory consumable storage device 10 is illustrated in FIGS. 1-13 in accordance with embodiments of the invention. The laboratory consumable storage device 10 comprises a main body 12 and a door 14 together forming an interior space or chamber. The chamber is divided into one or more storage compartments, each storage compartment for receiving a carrier holding a plurality of laboratory consumables to be sterilized, dried, and/or stored. The number of compartments, and therefore the number of carriers the device may hold at one time, may vary depending on many factors, such as the user's requirements, the space availability at the user's facility, the size of the carriers (which is dependent on the size and quantity of the laboratory consumables to be stored in each carrier), etc. The illustrated device 10 has nine compartments in a 3×3 arrangement. The devices may or may not be stackable. If the devices are stackable, it may be necessary to employ a spacer that maintains sufficient space between the stacked devices for adequate air flow.

It is typically desirable for the door, when closed, to adequately seal the chamber such that air is not sucked in around the door when optional ventilation fans (described below) are operated. In the illustrated embodiment, the door 14 has a magnetic gasket 16 around the perimeter of its internal side to provide such a desired seal. A sensor may be used to detect if the door is open, such that the device will not operate (e.g., the UV lamps will not be turned on) if the door is open. Further, an alarm or other indicator may be actuated if the door is left open for longer than a predetermined threshold time. An optional door locking mechanism (not illustrated), which may be controlled automatically, may be present.

A laboratory consumable storage device of embodiments of the invention will typically have a user interface 18, which may comprise one or more user input devices (e.g., buttons, switches, knobs, keypad, bar code reader, magnetic scanner, RFID scanner, etc.) and one or more user output devices (e.g., lights, LED or LCD displays, sound generators (such as buzzers or beepers), etc.). Any suitable number, type, arrangement, and location of user input and output devices may be used.

Figure 1:
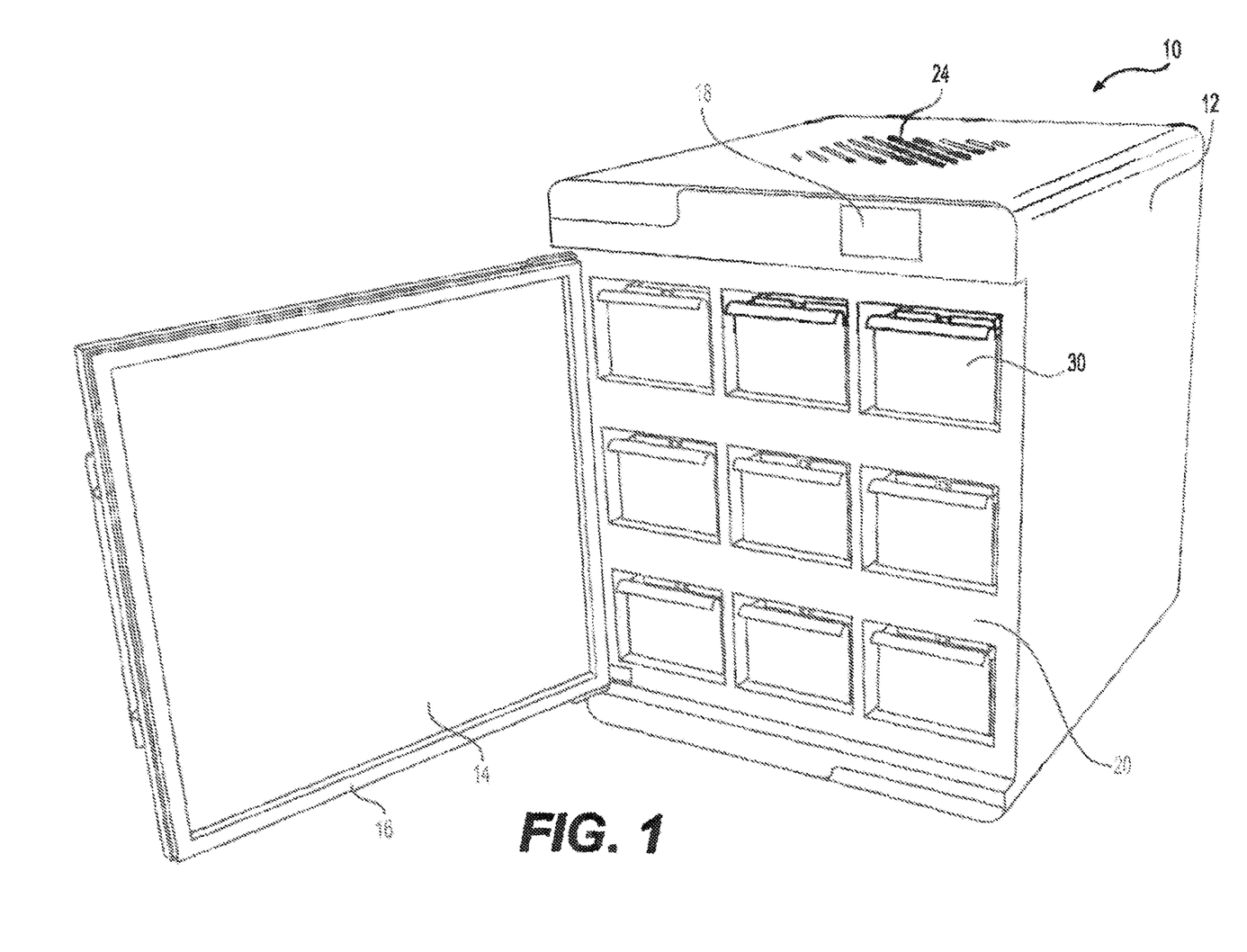
FIG. 1 illustrates a perspective view of a laboratory consumable sterilizing and storage device, in accordance with embodiments of the invention.
Figure 12:
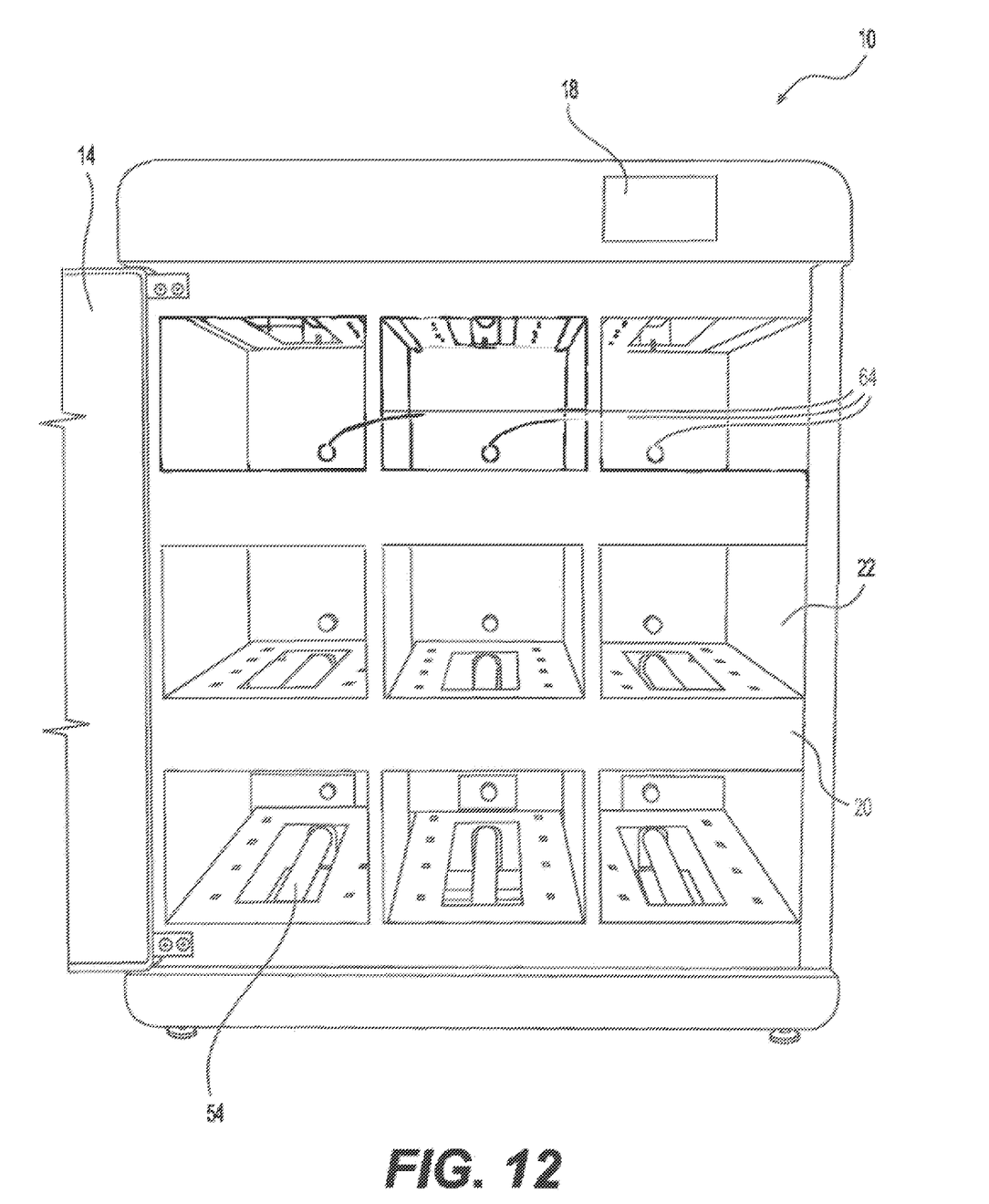
FIG. 12 illustrates a front view of the laboratory consumable sterilizing and storage device of FIG. 1 with the door open.

The laboratory consumable storage device 10 as illustrated has nine compartments for receiving and holding carriers holding laboratory consumables. FIG. 1 shows the device with carriers 30 in the compartments, while FIG. 12 shows the device with no carriers in the compartments. A faceplate 20 defines the openings 22 of the compartments through which the carriers are inserted. Indicia may be present (such as on the faceplate 20) to indicate reference numbers for each storage compartment. A light or other similar indicator may be adjacent each storage compartment, such as to provide a real-time indication to a user as to which storage compartment to insert a carrier into or remove a carrier from.

In the illustrated embodiment, the internal structure of the compartments is formed by U-shaped structures 40 that are arranged and mounted within the chamber of the device in the desired number and configuration. The U-shaped structures 40 are illustrated removed from the device for clarity in FIGS. 5-8. Such U-shaped structures are one exemplary way to form the storage compartments, however any suitable structure or mechanism may be used.

In the illustrated embodiment, the carriers 30 are manually slid into and out of the compartments by users as needed. In alternative embodiments of the invention (not illustrated), other mechanisms may be used for guiding or propelling the carriers into and out of the compartments. As an example, telescoping or extending guides or drawers may extend out of the compartments for loading/unloading of the carriers and retract into the compartments for storage. Such extension and retraction may be manual or powered. In the illustrated embodiment, the carriers 30 rest on the shelves 42 of the compartments when inserted into the compartments. In alternative embodiments of the invention (not illustrated), other mechanisms may be used for supporting or hanging the carriers within the compartments (for example, opposing horizontal support guides).

Figure 2:
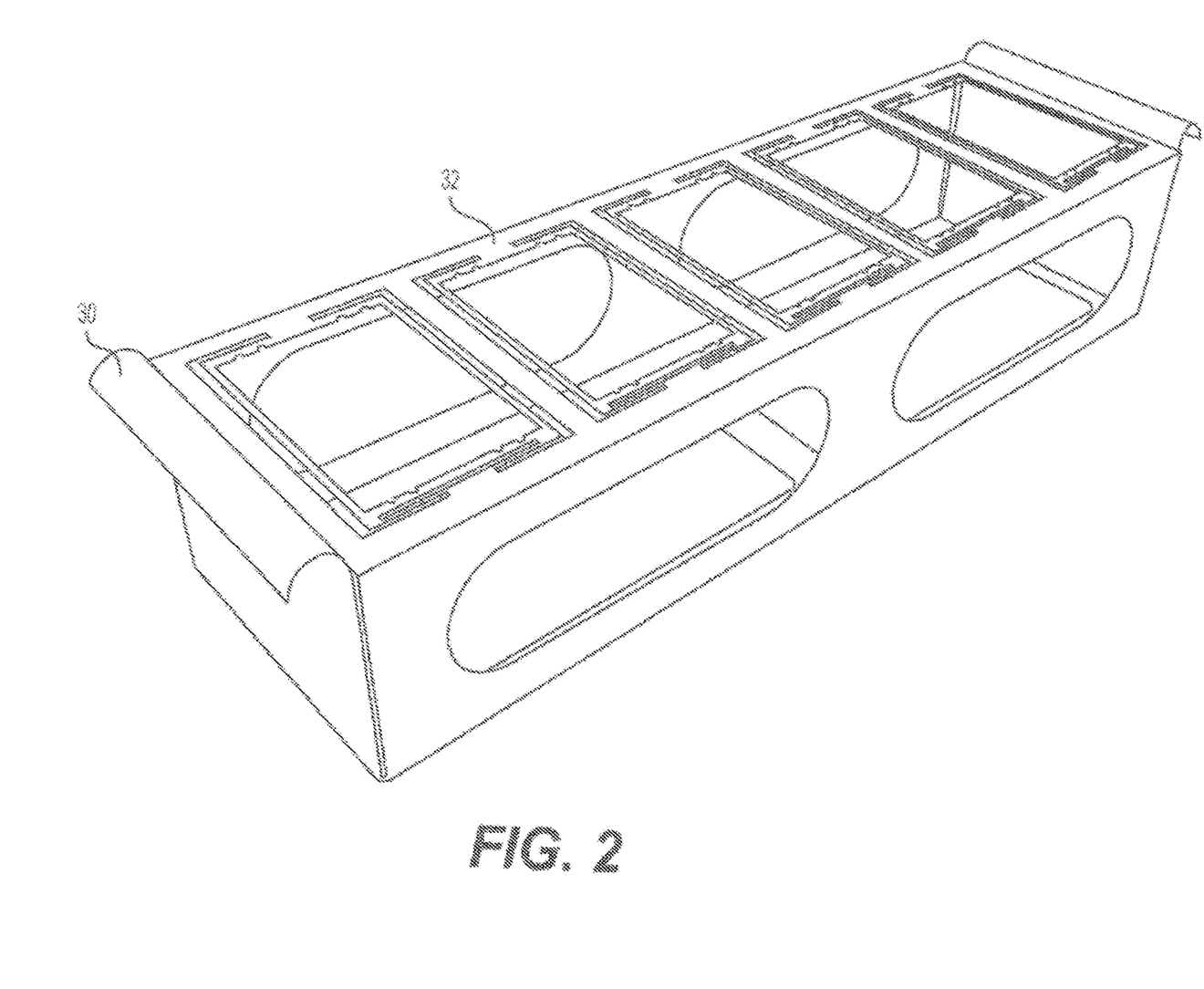
FIGS. 2-4 illustrate perspective views of tip rack carriers which may be used in conjunction with the laboratory consumable sterilizing and storage device of FIG. 1.
Figure 3:
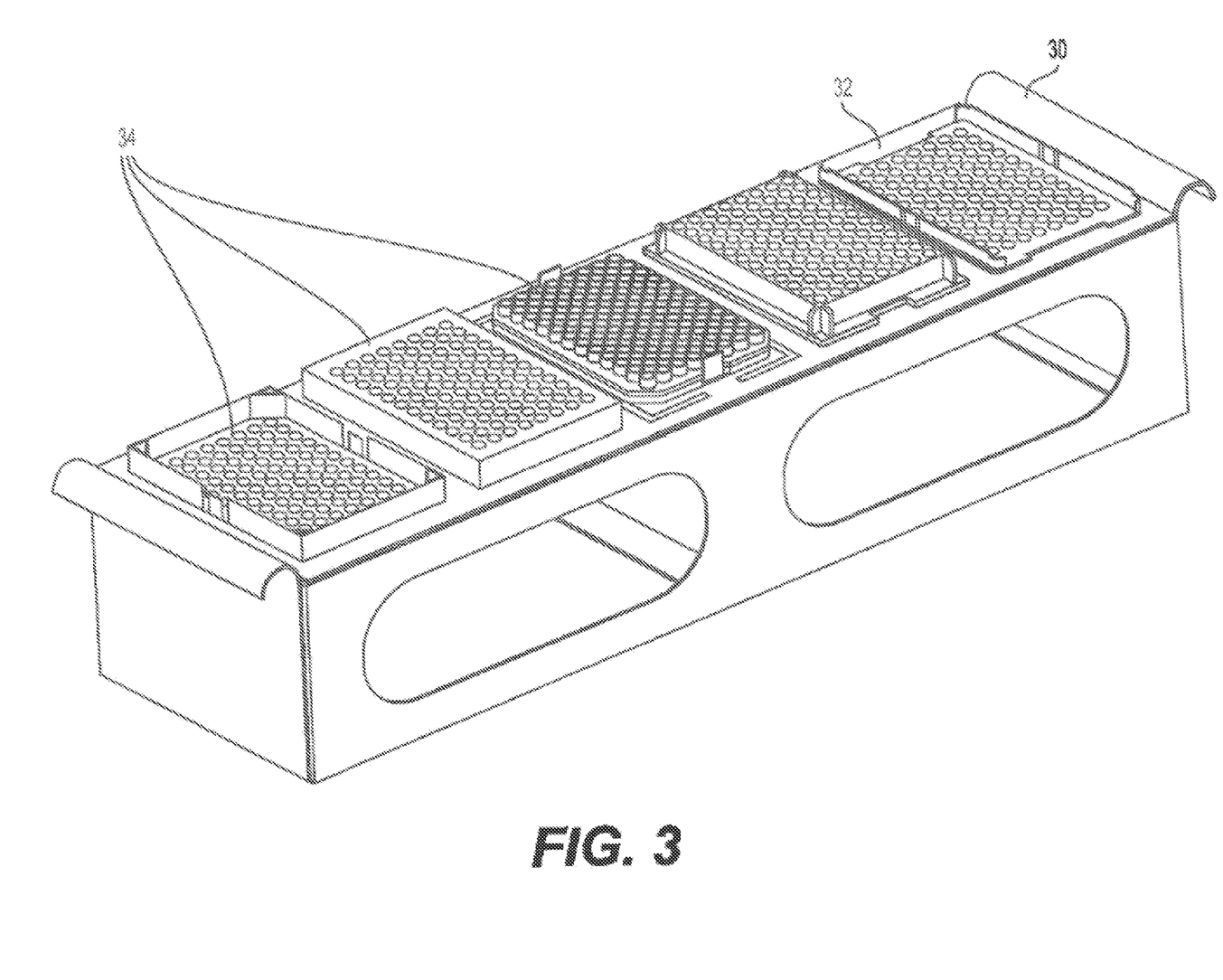
Figure 4:
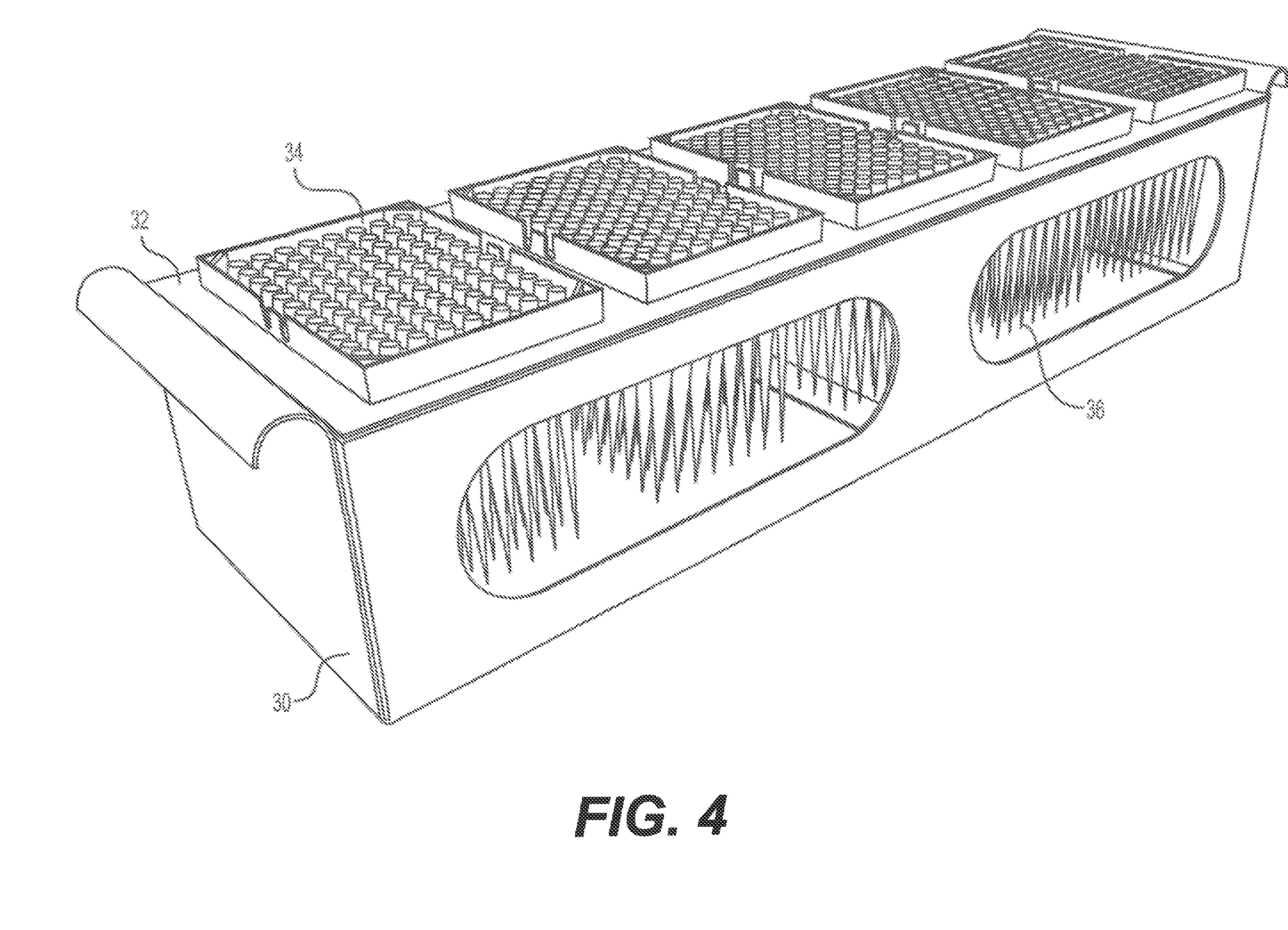

As seen in FIGS. 2-4, the carrier 30 comprises a frame having elongated sides with large openings, closed ends with handles, an open bottom, and a tip rack adapter plate 32 on top. The tip rack adapter plate 32 has a plurality of openings (five openings are illustrated, but the tip rack adapter plate may have more or fewer openings as needed). A tip rack 34 may be placed on the tip rack adapter plate 32 at each of the openings, such that the tip rack sits on the edges of the respective opening and the pipette tips in the tip rack protrude down through the respective opening. FIG. 2 shows a carrier with no tip racks in place and FIG. 3 shows a carrier with tip racks 34 in place at all five of the openings. The tip rack adapter 32 may be able to hold a variety of different tip racks 34 (the specific tip rack used will depend on the type and number of pipette tips to be stored). As seen in FIG. 4, the tip racks 34 each hold a plurality of pipette tips 36 (or other type of laboratory consumable). The number of pipette tips held by each tip rack may vary. The one or more tip racks 34 may hold 24, 48, 96, 384, or 1536 pipette tips, by way of example, although the one or more tip racks 34 may hold other numbers of pipette tips. The laboratory consumable storage device 10 may be utilized with pipette tips with volumes of 10 μL-5 mL, such as 10 μL, 50 μL, 1 mL, or 5 mL pipettes, by way of example, with corresponding lengths between 30 mm-120 mm, although the laboratory consumable storage device 10 may be utilized with pipette tips with other sizes and configurations. In the illustrated embodiment, each tip rack 34 holds 96 pipette tips 36. When the pipette tips 36 are in place in the tip racks 34 and the tip racks are in place on the tip rack adapter plate 32, the pipette tips 36 hang down into the interior of the carrier as seen in FIG. 4. The elongated sides of the carrier 30 have large openings which, along with the open bottom, enable UV light and air flow (described below) to readily reach the pipette tips. In the illustrated embodiment, both ends of the carrier 30 have top edges that curve out and down to form handles. Handles on both ends of the carrier may be desirable because the carrier typically is insertable into the compartments with either end first. Any other suitable type of handle mechanism may be used, on either or both ends of the carrier. Alternatively, the carrier may have no handles.

Figure 5:
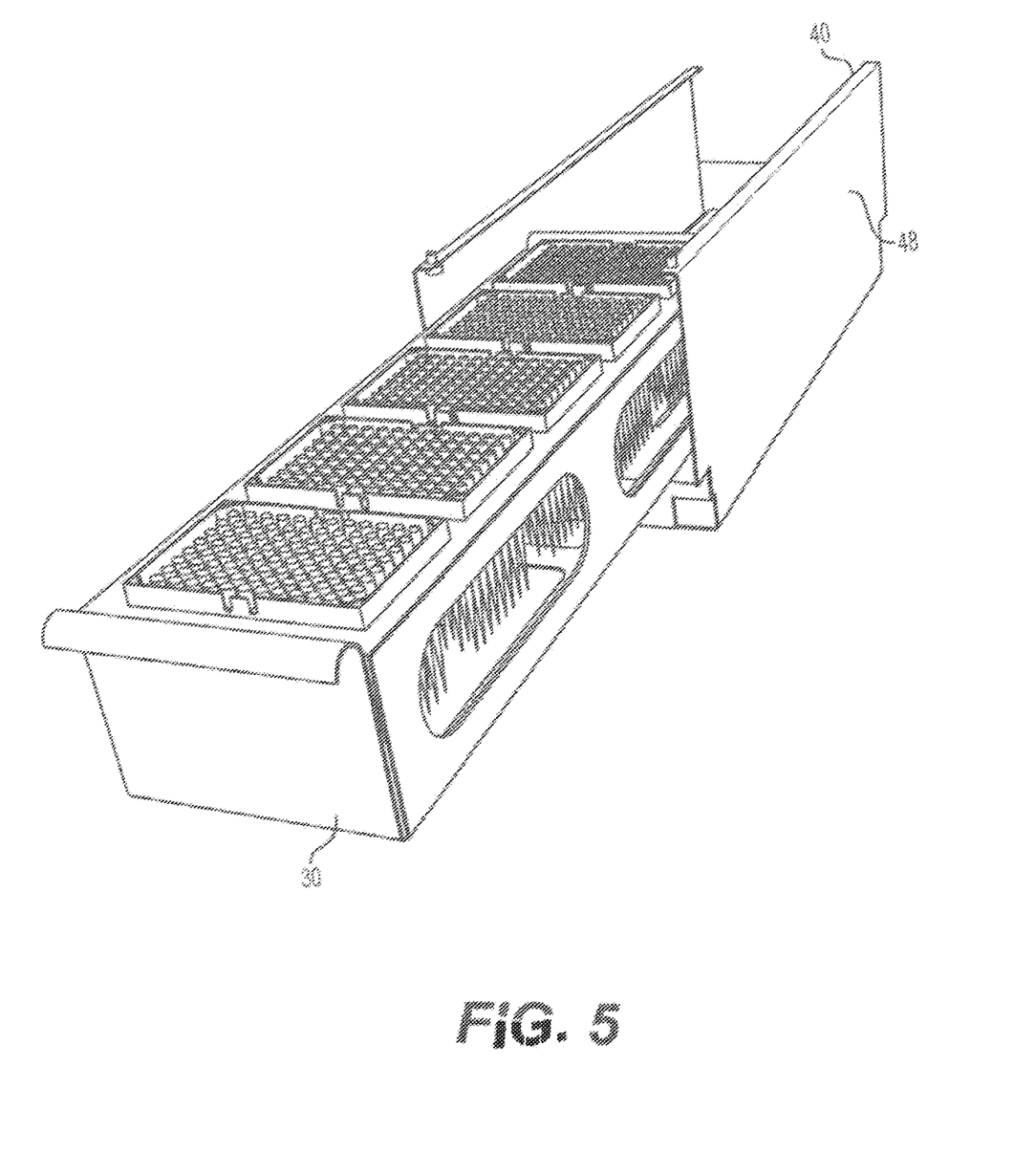
FIG. 5 illustrates a perspective view of how a tip rack carrier interfaces with a corresponding storage compartment of the laboratory consumable sterilizing and storage device of FIG. 1.
Figure 6:
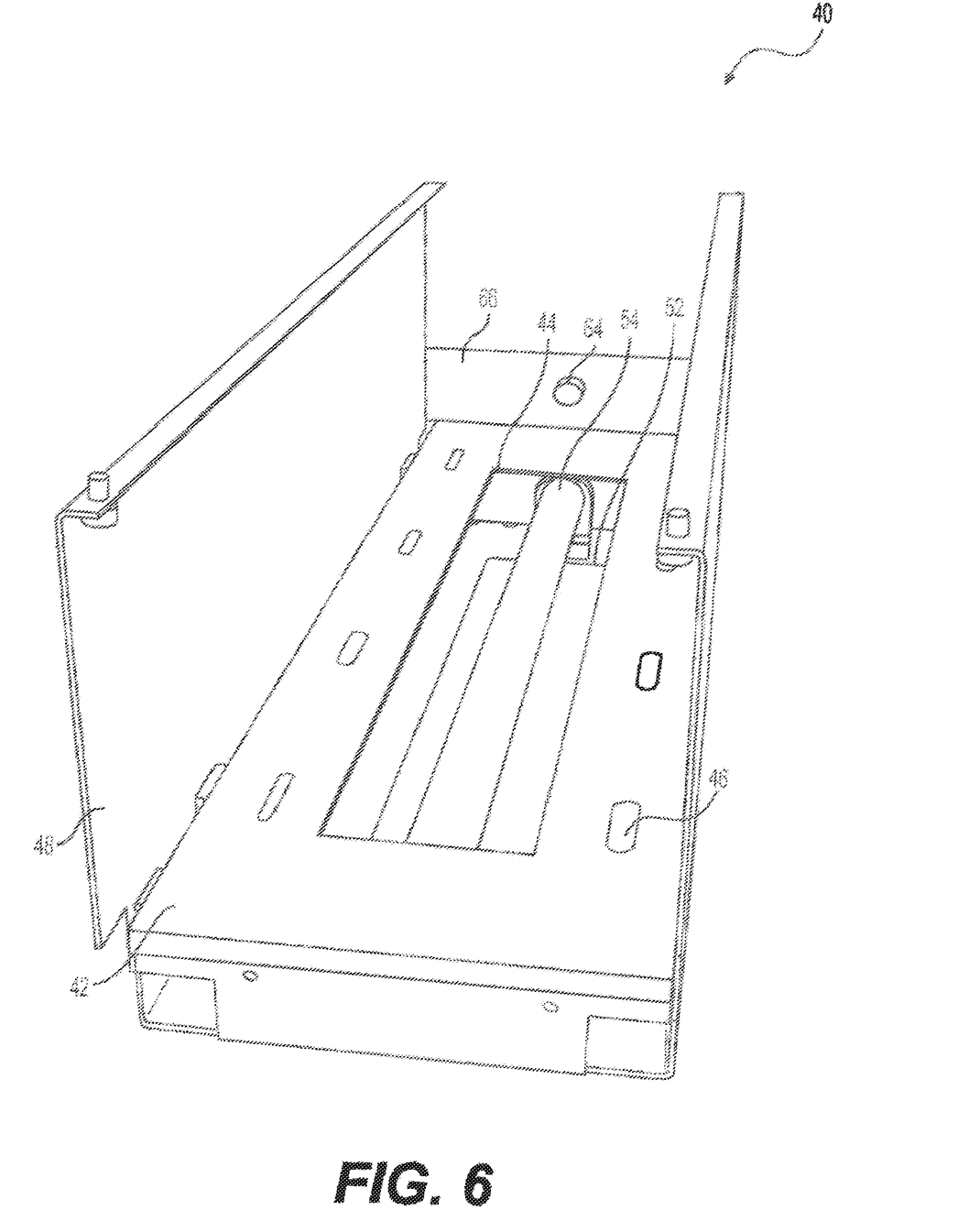
FIGS. 6 and 7 illustrate top perspective view of a storage compartment of the laboratory consumable sterilizing and storage device of FIG. 1.
Figure 7:
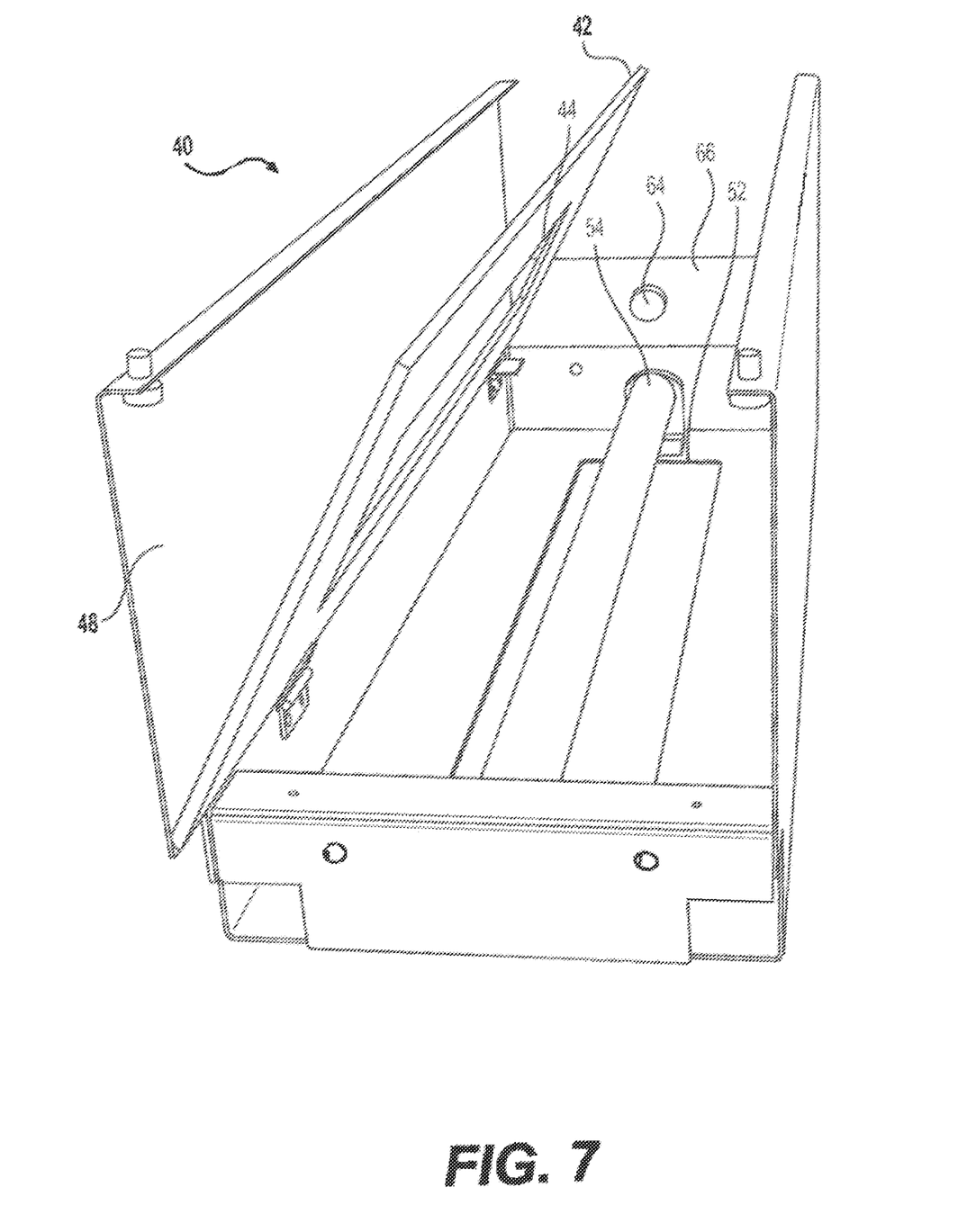
Figure 8:
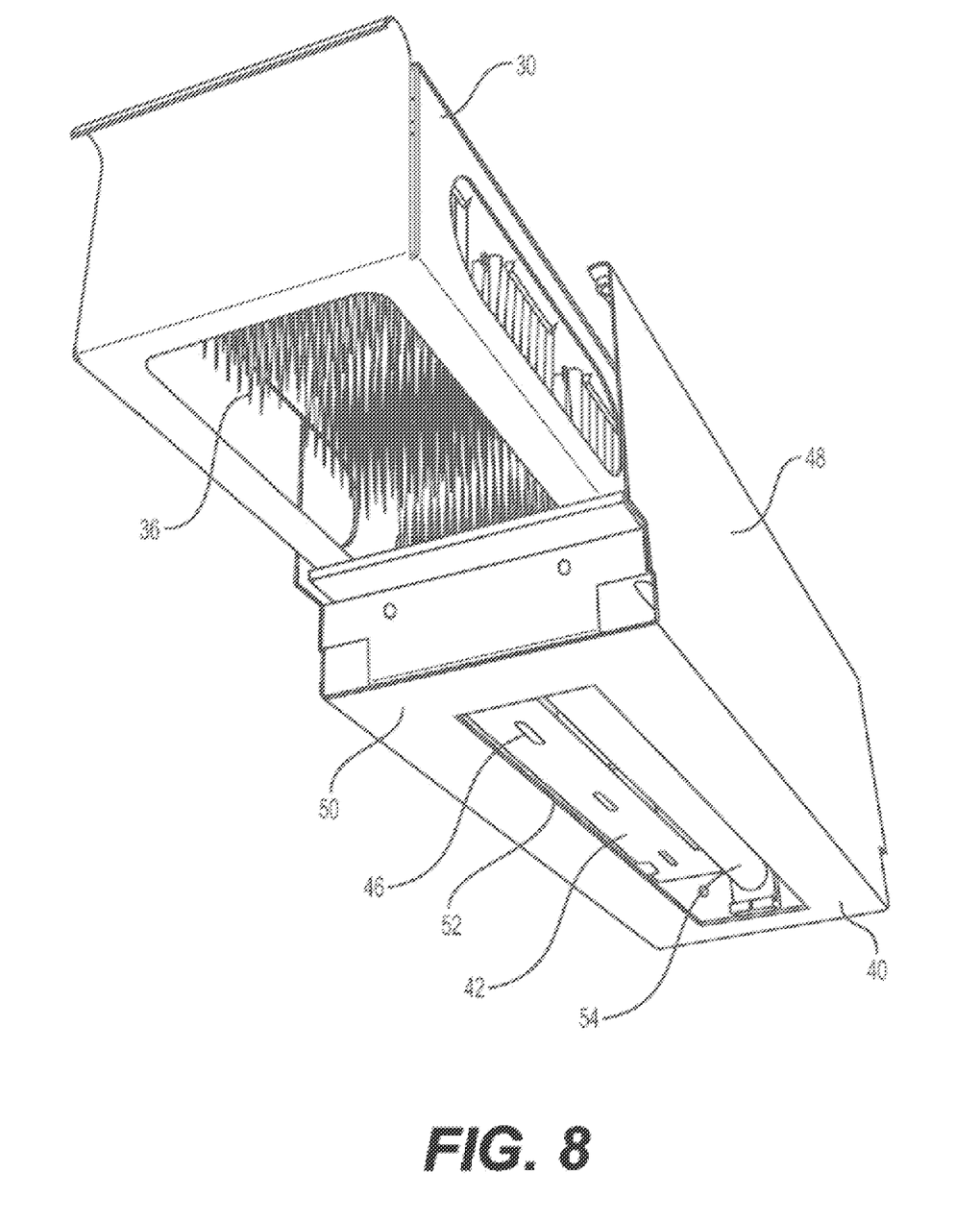
FIG. 8 illustrates a bottom perspective view of a storage compartment of the laboratory consumable sterilizing and storage device of FIG. 1.

Referring now to FIGS. 5-8, various views of a U-shaped structure 40 are illustrated, with the structure removed from the tip storage device 10 for clarity. Such U-shaped structures are one exemplary way to form the storage compartments in the laboratory consumable storage devices of embodiments of the invention, but any other suitable structure or mechanism may be used. FIG. 5 illustrates the U-shaped structure with a partially inserted carrier, and FIG. 6 illustrates the U-shaped structure with no carrier. The U-shaped structure 40 comprises opposing elongated walls 48 and a bottom chamber 50 for housing one or more UV lightbulbs 54 (also termed "lamps"). The bottom chamber 50 houses a UV lightbulb 54 for exposing the pipette tips to UV light in order to sanitize the pipette tips (or maintain sanitization of pipette tips that have already been sanitized). The bottom and top walls of the bottom chamber 50 each have elongated holes 52, 44 (respectively) that coincide with the UV lightbulb 54. Such elongated holes 52, 44 enable UV light emitted by the UV lightbulb 54 to project upward onto the pipette tips held in the respective U-shaped structure and downward onto the pipette tips held in the U-shaped structure below. If a different number of UV lightbulbs and/or differently shaped UV lightbulbs are used, as may be the case, then the number and shape of the holes in the bottom and top walls of the UV chamber may vary accordingly. The top wall 42 of the bottom chamber 50 (which forms a shelf on which a carrier sits) may be hinged (as illustrated in FIG. SB) to enable easy access to the UV lightbulb 54 for maintenance and replacement. In an alternative embodiment (not illustrated), the top wall of the bottom chamber may be completely separable, such as by lifting or sliding, and may be secured using any suitable securing device or mechanism (e.g., screws or bolts). Any other suitable structure or mechanism for enabling access to the UV lightbulb 54 for maintenance and replacement may be used. As seen in FIG. 6, a plurality of holes 46 may be defined in the top wall 42 of the bottom chamber, on opposing sides of hole 44, to facilitate air flow through the device to help dry the pipette tips.

It may be desirable to determine which storage compartment contains a tip rack carrier. As such, laboratory consumable storage devices of embodiments of the invention may comprise one or more sensors capable of detecting the presence of a carrier in each storage compartment. As seen in FIGS. 6 and 12, the sensors 64 may be mounted on the back wall 66 of each of the nine storage compartments. Any suitable type, number, and location of proximity sensor may be used.

Figure 9:
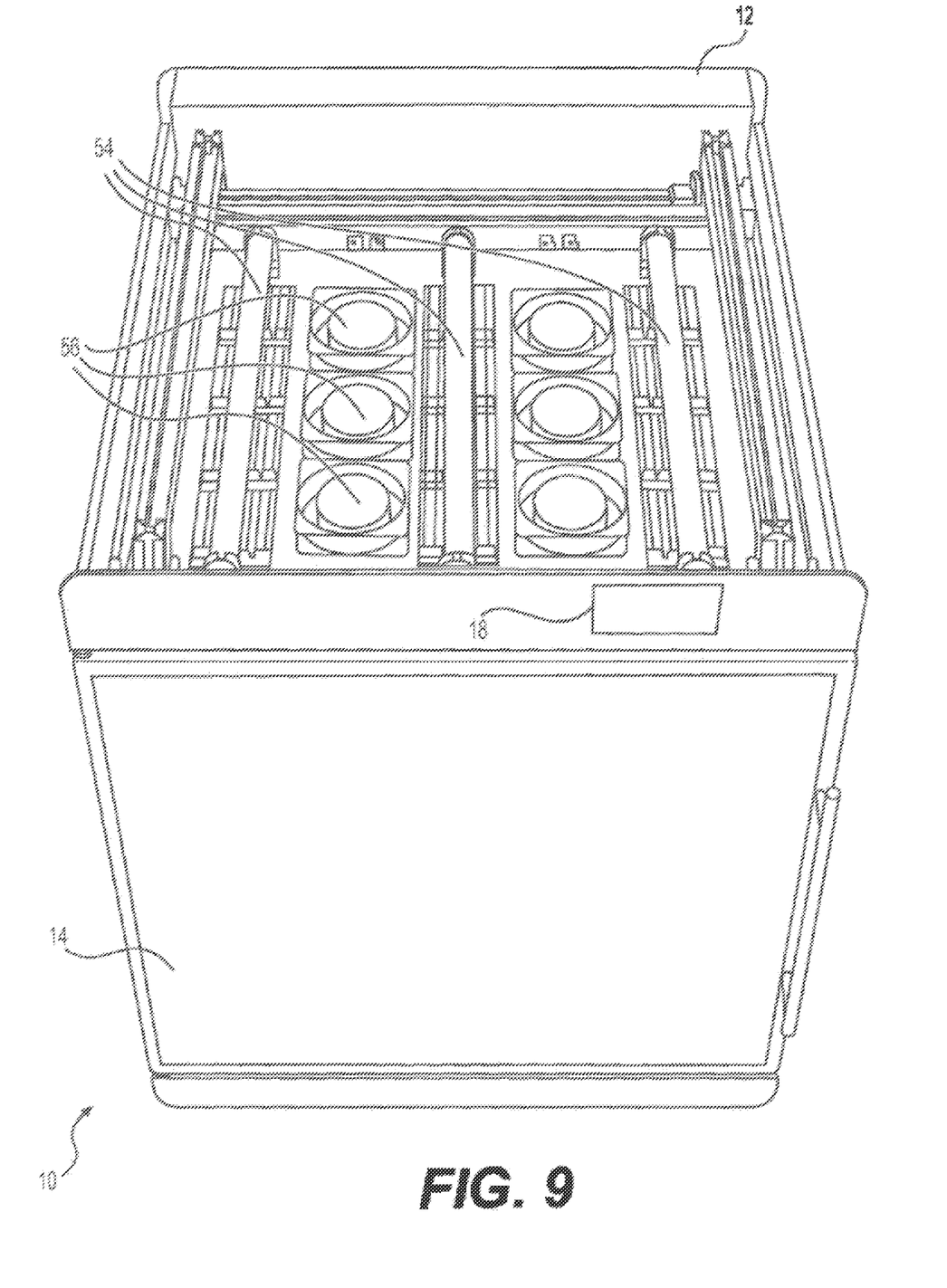
FIGS. 9 and 10 illustrate top perspective views of the laboratory consumable sterilizing and storage device of FIG. 1 with the top panel removed.
Figure 10:
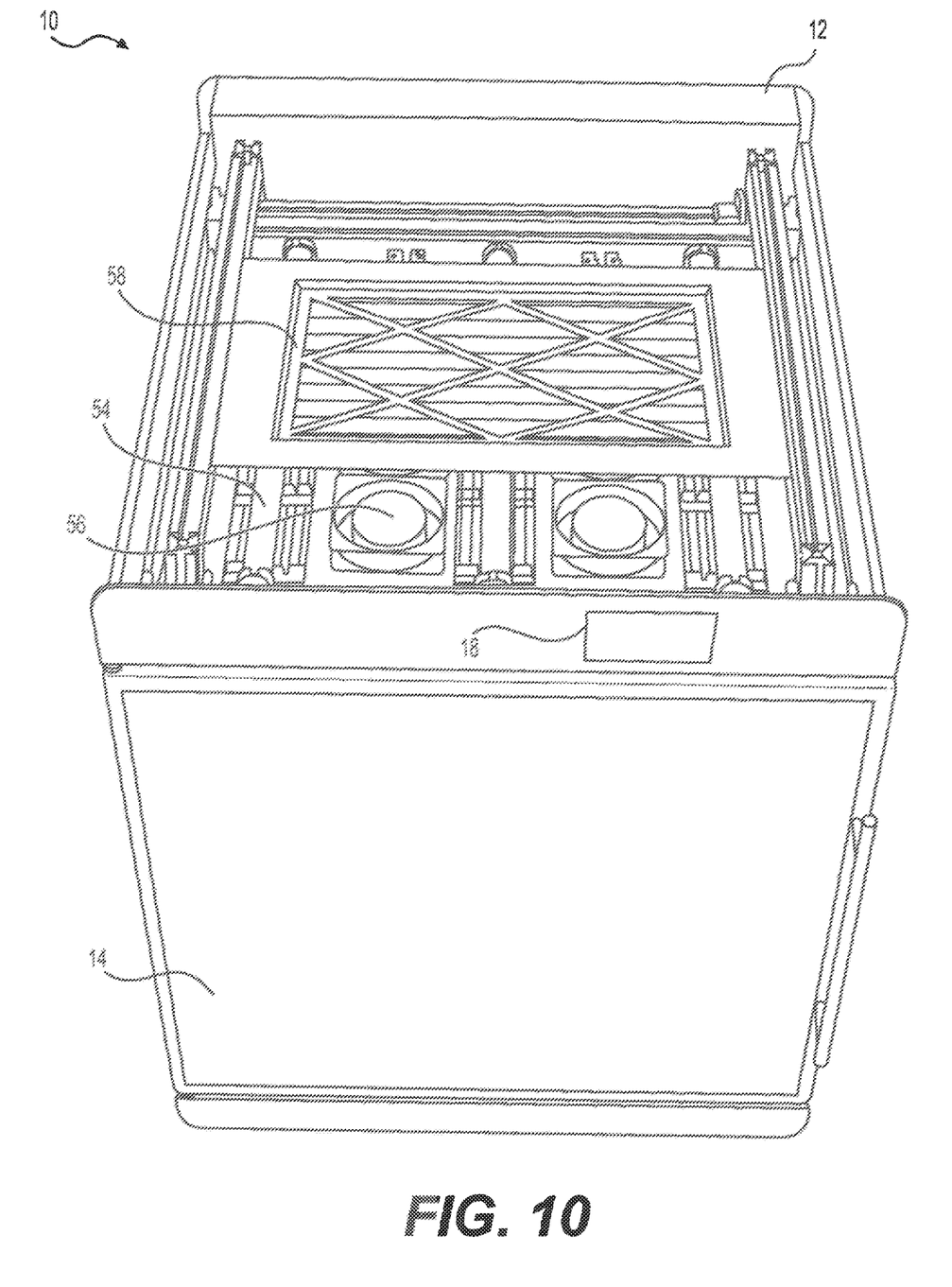
Figure 11:
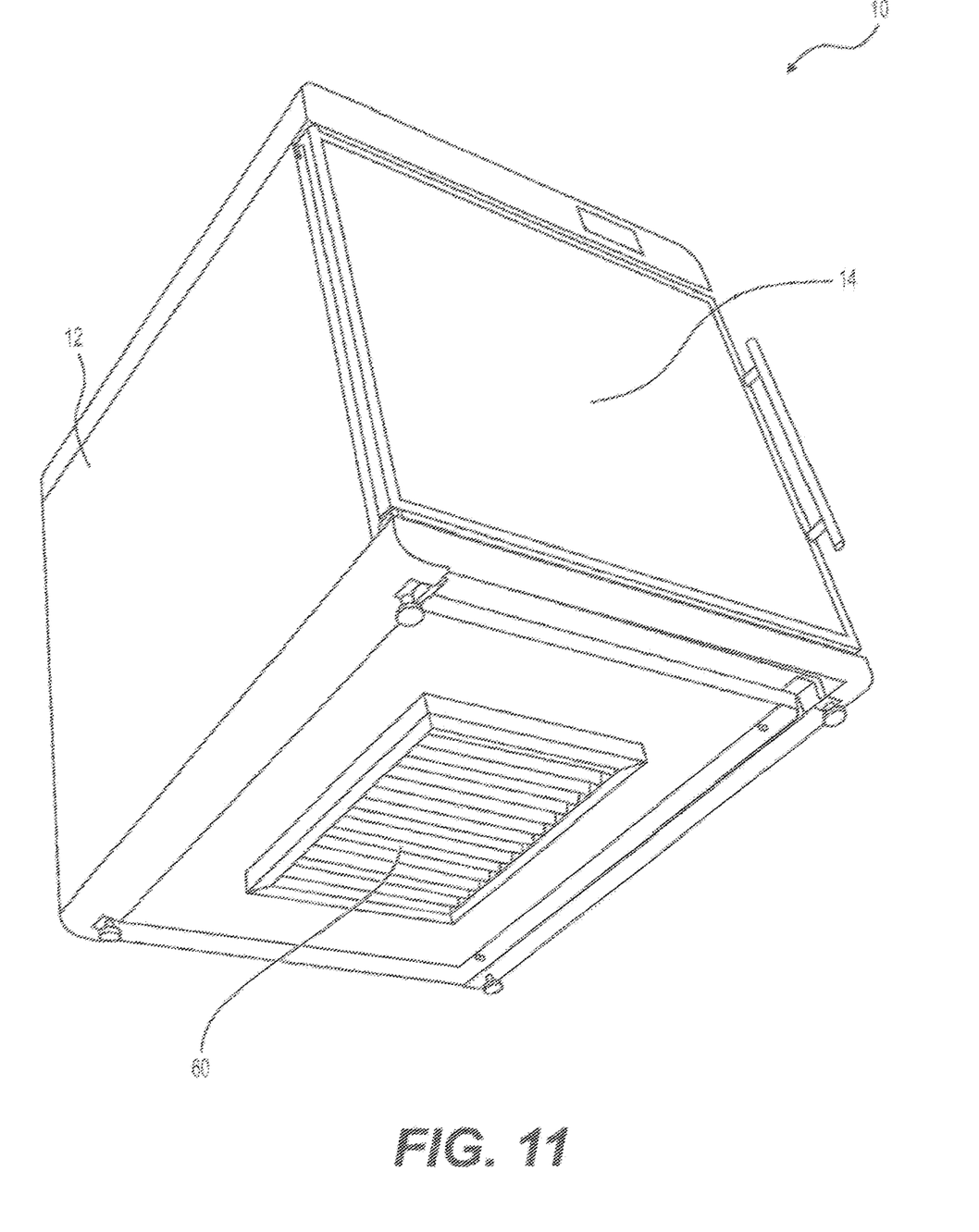
FIG. 11 illustrates a bottom perspective view of the laboratory consumable sterilizing and storage device of FIG. 1.

In addition to the UV lightbulbs in the bottom chamber 50 of the U-shaped structure, one or more additional UV lightbulbs may be mounted in other locations to ensure adequate exposure of UV light to the pipette tips. For example, the laboratory consumable storage device 10 comprises three additional UV lightbulbs mounted in the top portion of the device, above the storage compartments (as seen in FIG. 9). These UV lightbulbs mounted in the top portion of the device help ensure that the tops of the pipette tips stored in the top storage compartments are exposed to UV light.

The UV lightbulb is an optional feature of the laboratory consumable storage devices of embodiments of the invention. If such a UV lightbulb is omitted from the device, the U-shaped structure may not require and thus may not have a bottom chamber, but rather may have a simple bottom wall. Such a bottom wall would typically have a plurality of ventilation holes, similar to holes 46 but likely more numerous to ensure adequate ventilation if elongated hole 44 is omitted. Alternatively, if such a UV lightbulb is omitted from the device, the same U-shaped structure may be used (for simplicity of manufacturing and cost reduction) but with the UV lightbulb and associated mounting/wiring hardware omitted.

Any suitable mechanism or structure may be used to mount the U-shaped structure in the device. In the illustrated embodiment, the top edges of the opposing walls are bent over 90 degrees and have bolt holes for bolting the U-shaped structure to beams (not illustrated) or any other suitable structure within the chamber of the device.

It may be desirable for laboratory consumable storage devices of embodiments of the invention to have the capability to dry the stored pipette tips, if needed. As such, the laboratory consumable storage devices of embodiments of the invention may include one or more ventilation fans that move air through (i.e., pull air into and push air out of) the storage device. Referring now to FIG. 9, the laboratory consumable storage device 10 comprises one or more (six are illustrated) ventilation fans 56 mounted in the top portion of the device, above the storage compartments (as seen in FIG. 6) (although other mounting locations may be used). Any suitable number, position, and capacity of fans may be used (typically varying based on the size of the laboratory consumable storage device). In one specific embodiment, 6 volt DC ventilation fans 56 are used. Such ventilation fans may be fixed or variable speed, and may be powered by AC or DC voltage. Such ventilation fans may be wired to all operate at the same time, or to be separately controlled for variable air flow through the device.

In alternative embodiments of the invention, one or more ventilation fans may be mounted at the bottom of the device (instead of or in addition to the fans at the top). In other alternative embodiments of the invention, one or more ventilation fans may be mounted on one or both sides, and/or on the back side of the device. In the illustrated embodiment of the invention, the ventilation fans are arranged to pull air into the bottom of the device 10 and push air out of the top of the device. In alternative embodiments of the invention, the ventilation fans may be arranged to pull air into the top of the device and push air out of the bottom of the device. In other alternative embodiments of the invention, the ventilation fans may be arranged to pull air into one side of the device and out of an opposite side of the device, thereby providing horizontal air flow through the device. Many other arrangements of fan number and position and of air flow may be provided and are within the scope of this disclosure.

An air filter 58 (seen in FIG. 10) may be mounted above the fans to filter the air leaving the device. Such a filter 58 may be enclosed within the main body 12 of the device and aligned with ventilation holes 24 (seen in FIG. 1) in the main body to enable the air to leave the device. Another air filter 60 (seen in FIG. 11) may be mounted at the bottom of the device to filter air being drawn into the device. Such a filter 60 may be mounted within the bottom wall of the device such that ventilation holes are not needed (such a method of mounting may be termed "flush-mounted"). While outgoing air filter 58 is illustrated as being enclosed and incoming air filter 60 is illustrated as being flush-mounted, either filter may be enclosed or flush-mounted. One or both of the air filters may be omitted. However, the incoming air filter 60 is typically more important to help prevent contamination of the stored pipette tips. One or both of the filters may be a HEPA filter or the like.

The ventilation fan(s) is/are an optional feature of the laboratory consumable storage devices of embodiments of the invention. If such a ventilation fan(s) is/are omitted from the device, the above-described filters and ventilation holes may or may not also be omitted.

In addition to the drying capability provided by the ventilation fans, additional drying capability may be provided by including one or more heaters the laboratory consumable storage devices of embodiments of the invention. Although not illustrated, the laboratory consumable storage device of embodiments of the invention may comprise one or more heater mounted in the rear portion of the device (although other mounting locations may be used). Such heaters would typically, although not necessarily, be mounted near the bottom of the device since hot air rises. Any suitable number, position, and capacity of heaters may be used (typically varying based on the size of the laboratory consumable storage device). In one specific embodiment, 400 watt heating fan heaters are used. Such heaters may have a fixed or variable output, and may be thermostatically controlled. Such heaters may be wired to all operate at the same time, or to be separately controlled for variable heating of the interior of the device.

Figure 13:
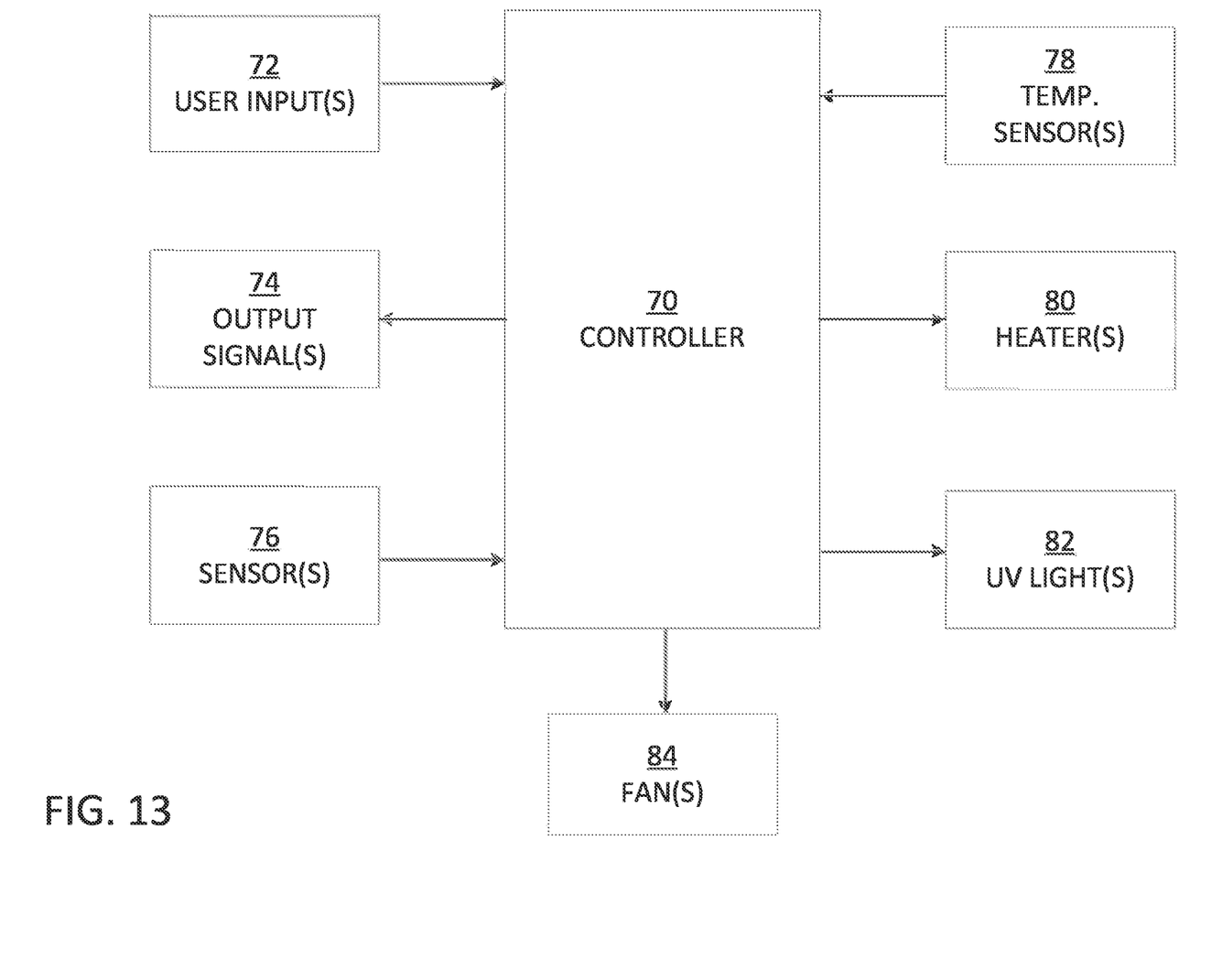
FIG. 13 illustrates a control system of a laboratory consumable sterilizing and storage device, in accordance with embodiments of the invention.

Referring now to FIG. 13, a control system of a laboratory consumable storage device is illustrated in accordance with embodiments of the invention. The laboratory consumable storage device 10 comprises a controller 70. The controller 70 may comprise a microprocessor, dedicated or general purpose circuitry (such as an application-specific integrated circuit or a field-programmable gate array), a suitably programmed computing device, or any other suitable means for controlling the operation of the storage device 10. The controller 70 may receive inputs from one or more user inputs devices 72, such as buttons, switches, knobs, keypad, bar code reader, magnetic scanner, RFID scanner, etc. The controller 70 may provide outputs to one or more output devices, such as lights, LED or LCD displays, sound generators (such as buzzers or beepers), etc. The controller may receive inputs from one or more sensors 76, such as proximity sensors that detect the presence of a carrier in each storage compartment and/or a door sensor that detects if the door is open. The controller 70 may receive inputs from one or more temperature sensors 78. The controller 70 may turn on and off one or more heaters 80, UV lights 82, and/or fans 84.

A method for storing and optionally disinfecting and/or drying pipette tips using the laboratory consumable storage device 10 will be described with reference to the figures. A user places either washed or new pipette tips 36 arranged in one or more tip racks 34 into a tip carrier 30 and slides the tip carrier 30 into one of the nine (in the illustrated embodiment) storage compartments. The proximity sensor 64 within that storage compartment will detect the present of the carrier. The user may then be prompted via the user interface 18 to confirm that a predefined sterilization procedure should be commenced. Such a predefined sterilization procedure would turn on the UV bulbs 54 corresponding to that specific storage compartment (e.g., the UV bulb above and the UV bulb below the specific storage compartment) for a predefined period of time. If the user does not answer or confirm within a predefined time after closing the door of the unit, then the sterilization procedure may automatically start for that storage compartment. If present, such an auto-start feature may be enabled or disabled by accessing the setting features on the user interface 18. As the sterilization and/or drying procedures are typically (but not necessarily) activated individually for each storage compartment, sterilization procedures may be running in multiple storage compartments at the same time, and may be at different stages (having different start and stop times) at any given time. When a carrier is inserted into a storage compartment, the sterilization and/or drying procedure for that storage compartment may be executed independently of whatever procedures are running in the other storage compartments.

Multiple different types of procedures may be available, such as different duration sterilization procedures, a combined sterilization and drying procedure that activates both the required UV bulbs 54 and one or more of the heating elements 62 and/or fans 56, or a drying only procedure that activates only one or more of the heating elements 62 and/or fans 56. Which procedure is to be used when a carrier is inserted may be set systematically, such as via the setting feature on the user interface, or may be selected individually via the user interface each time a carrier is inserted. A sterilization procedure may optionally be commenced in all of the storage compartments anytime the door is opened (such a precautionary sterilization procedure may have a shorter duration than the standard sterilization procedure).

The sterilization procedure will only execute (and therefore the UV bulbs will only be on) when the door 14 to the unit is fully closed. If, at any point the door is opened, the controller 70 will turn off all the UV bulbs to avoid any harm to the user. When the door is re-closed, the sterilization procedure (or procedures, if running in multiple compartments) will typically resume and continue executing until the predetermined procedure runtime is reached (optionally, additional time may be added to each procedure that was paused). Such a pause and resumption may occur if the door is opened to insert a carrier or to remove a carrier (or both).

An indicator (or indicators) may be provided to the user of which storage compartment(s) the sterilization procedure has completed and therefore from which storage compartment(s) the carrier and tips may be removed for use. Such an indicator may be provided on the user interface 18, or in any other suitable manner (as another example, indicator lights (e.g., red and green) may be provided adjacent each storage compartment to indicate whether the carrier within may be removed). The indicator(s) may indicate all of the storage compartments in which the sterilization procedure has completed and therefore any of the indicated carriers can be removed. Alternatively, the indicator(s) may indicate only the one storage compartment in which the sterilization procedure has been completed for the longest time (thereby providing a first-in, first-out (FIFO) system). If a carrier is removed prior to the completion of its sterilization procedure (as detected by the proximity sensor), a warning will typically be provided to the user (via the user interface, or any other suitable mechanism or method). The user may then be provided an option to re-insert the carrier and restart the sterilization procedure or to ignore (i.e., dismiss) the warning.

Some or all the activities, such as the insertion and removal of carriers, may be recorded and may be viewable on the user interface and/or downloadable to a separate computer/server or the like.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A sterilizing and storage device comprising:
a housing defining an interior chamber and having an opening defined in the housing to enable access to the interior chamber, the interior chamber divided into a plurality of storage compartments, each storage compartment adapted to slidably receive a carrier holding a plurality of laboratory consumables;
a door affixed to the housing and selectively movable between a closed position closing off the opening and an open position enabling access to the interior chamber and the storage compartments;
a plurality of ultraviolet (UV) lamps positioned such that each storage compartment receives UV light from a UV lamp;
one or more fans to draw air into the housing;
a plurality of carriers, each carrier adapted to hold a plurality of laboratory consumables suspended from an upper surface of the carrier such that a distal end of each of the plurality of laboratory consumables hangs down into an open interior portion of the carrier, each carrier having one or more side surface openings defined therein and one or more bottom surface openings defined therein to enable air flow and UV light to reach the distal ends of the plurality of laboratory consumables, each of the plurality of carriers includes a frame having an open bottom and openings along sides thereof enabling UV light and air flow to readily reach the laboratory consumables, each of the plurality of carriers also includes a tip rack adapter plate, the tip rack adapter plate includes a plurality of openings upon which a tip rack may be placed such that the tip rack sits on edges of the respective opening and the laboratory consumables in the tip rack protrude down through the respective opening;
a controller for controlling operation of the storage device; and
a plurality of carrier sensors in communication with the controller, each carrier sensor positioned for detecting a presence of a carrier in a respective storage compartment, wherein the controller activates only the UV lamps positioned adjacent the storage compartments in which the presence of a carrier has been detected.

2. The sterilizing and storage device of claim 1, further comprising:
a door sensor in communication with the controller for detecting whether the door is open or closed.

3. The sterilizing and storage device of claim 2, wherein the controller activates one or more UV lamps after one or more carriers have been detected to have been inserted into respective storage compartments and the door has been detected to be closed.

4. The sterilizing and storage device of claim 3, wherein the controller activates the 5. UV lamps for a predetermined amount of time.

5. The sterilizing and storage device of claim 4, wherein the controller deactivates the UV lamps if the door has been detected to be opened and the controller reactivates the UV lamps when the door has been detected to be closed.

6. The sterilizing and storage device of claim 3, wherein the controller determines if a carrier has been removed prior to completion of a predefined sterilization procedure and provides a notification to a user.

7. The sterilizing and storage device of claim 1, further comprising an air intake defined in one wall of the housing and an air outflow defined in an opposing wall of the housing, wherein the one or more fans to draw air into the housing through the air intake, through the interior chamber, and out of the housing through the air outflow.

8. The sterilizing and storage device of claim 1, further comprising one or more heaters for providing heat to the interior chamber.

* * * * *